US009953385B2

(12) United States Patent
Lougheed et al.

(10) Patent No.: US 9,953,385 B2
(45) Date of Patent: Apr. 24, 2018

(54) SYSTEM AND METHOD FOR MEASURING HEALTHCARE QUALITY

(75) Inventors: Charlie Lougheed, Shaker Heights, OH (US); Anil Jain, Solon, OH (US); Doug Meil, Chagrin Falls, OH (US); Brad Jarrell, Avon, OH (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 547 days.

(21) Appl. No.: 13/556,640

(22) Filed: Jul. 24, 2012

(65) Prior Publication Data
US 2014/0032240 A1    Jan. 30, 2014

(51) Int. Cl.
| G06Q 10/00 | (2012.01) |
| G06Q 50/00 | (2012.01) |
| G06Q 50/24 | (2012.01) |
| G06Q 10/10 | (2012.01) |
| G06F 19/00 | (2018.01) |

(52) U.S. Cl.
CPC .......... *G06Q 50/24* (2013.01); *G06F 19/327* (2013.01); *G06Q 10/10* (2013.01)

(58) Field of Classification Search
CPC ....... G06Q 50/22; G06Q 50/24; G06F 19/322
See application file for complete search history.

(56) References Cited

U.S. PATENT DOCUMENTS

| 6,725,250 | B1 * | 4/2004 | Ellis ..................... A01N 25/30 |
| | | | 705/30 |
| 2003/0195772 | A1 * | 10/2003 | Meek .................... G06Q 10/10 |
| | | | 705/2 |
| 2010/0241445 | A1 * | 9/2010 | Rago et al. ................ 705/2 |
| 2012/0035948 | A1 * | 2/2012 | Borton .................. G06Q 50/22 |
| | | | 705/2 |
| 2012/0065998 | A1 * | 3/2012 | George et al. .............. 705/3 |
| 2012/0116985 | A1 * | 5/2012 | Rastogi ..................... 705/317 |
| 2012/0253835 | A1 * | 10/2012 | Tracy et al. .................. 705/2 |

* cited by examiner

*Primary Examiner* — Christopher L Gilligan
(74) *Attorney, Agent, or Firm* — Ryan Lewis; Edell, Shapiro & Finnan, LLC

(57) ABSTRACT

In a method for measuring healthcare quality, a plurality of computers operating in parallel receive from a patient dataset representative of patients within a healthcare organization, the patient dataset being distributed across the plurality of computer as subsets of patient datasets. The plurality of computers receive at least one healthcare quality measure definition comprising a numerator and a denominator. The plurality of computers identify, in the subsets of patient datasets, patient data that corresponds to the measure definition. The plurality of computers attribute the identified patient data to at least one provider based on an attribution rule. The plurality of computers calculate at least one healthcare quality measure for the at least one provider, according to the healthcare quality measure definition, based on the attributed patient encounters. The plurality of computers store the at least one calculated healthcare quality measure in a measure dataset.

20 Claims, 6 Drawing Sheets

SYSTEM AND METHOD FOR MEASURING HEALTHCARE QUALITY

FIELD OF INVENTION

The present disclosure relates to the field of healthcare data management. More particularly, the present invention relates to aggregating healthcare data to measure healthcare quality.

BACKGROUND

Quality of healthcare being provided within healthcare organizations may drive the organizations' success in terms of profitability and patient satisfaction. Accordingly, healthcare organizations collect and analyze large amounts of data in order to measure the performance of affiliated healthcare providers, which in turn enables the healthcare organizations to track the quality of healthcare being delivered to patients. Additionally, by monitoring performance of affiliated healthcare providers, healthcare organizations are able to ensure that they meet certain requirements in order to receive funding such as a grants, incentives, and reimbursements. The National Quality Forum, for example, defines certain quality standards which are adopted by various insurance programs such as Medicare. A healthcare organization may not be eligible for reimbursement from an insurance program like Medicare unless it meets defined quality standards.

Collecting and analyzing data in order to track healthcare quality may be difficult for a healthcare organization, particularly for a large organization having many providers operating under several sub-organizations within the organization. For example, a healthcare organization may include several hospitals. Within each hospital, patients may visit a number of different doctors, or providers. Moreover, the patients may visit multiple hospitals. Additionally, different providers or hospitals may collect and store data in different formats. Thus, large amounts of healthcare data may be diverse and scattered across many different systems throughout a healthcare organization. Moreover, performing numerous complex calculations across large amounts of data may be time consuming. As a result, efficiently measuring healthcare quality using a holistic enterprise approach may be difficult.

SUMMARY OF THE INVENTION

In a method for measuring healthcare quality, a plurality of computers operating in parallel receive a patient dataset representative of patients within a healthcare organization, the patient dataset being distributed across the plurality of computers as subsets of patient datasets. The plurality of computers receive at least one healthcare quality measure definition comprising a numerator and a denominator. The plurality of computers identify, in the subsets of patient datasets, patient data that corresponds to the measure definition. The plurality of computers attribute the identified patient data to at least one provider based on an attribution rule. The plurality of computers calculate at least one healthcare quality measure for the at least one provider, according to the healthcare quality measure definition, based on the attributed patient data. The plurality of computers store the at least one calculated healthcare quality measure in a measure dataset.

A system for measuring healthcare quality includes at least one processor, at least one computer-readable tangible storage device, and program instructions stored on the at least one storage device for execution by the at least one processor. The program instructions include first program instructions configured to receive a patient dataset representative of patients within a healthcare organization. The program instructions further include second program instructions configured to receive at least one healthcare quality measure definition a numerator representative of a first patient encounter definition and a denominator representative of a second patient encounter definition. The program instructions further include third program instructions configured to identify, in the patient dataset, patient data that corresponds to the measure definition. The program instructions further include fourth program instructions configured to attribute the identified patient data to at least one provider based on an attribution rule. The program instructions further include fifth program instructions configured to calculate at least one healthcare quality measure for the at least one provider, according to the healthcare quality measure definition, based on the at least one attributed patient encounter. The program instructions further include sixth program instructions configured to store the at least one calculated healthcare quality measure in a measure dataset.

A computer program product for measuring healthcare quality includes at least one computer-readable tangible storage device and program instructions stored on the at least one storage device. The program instructions include first program instructions configured to receive at least one healthcare quality measure definition comprising a numerator representative of a first patient encounter definition and a denominator representative of a second patient encounter definition. The program instructions further include second program instructions configured to identify patient data that correspond to the measure definition. The program instructions further include third program instructions configured to attribute the identified patient data to at least one provider based on an attribution rule. The program instructions further include fourth program instructions configured to calculate at least one healthcare quality measure for the at least one provider, according to the healthcare quality measure definition, based on the at least one attributed patient encounter.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

Figure 1:
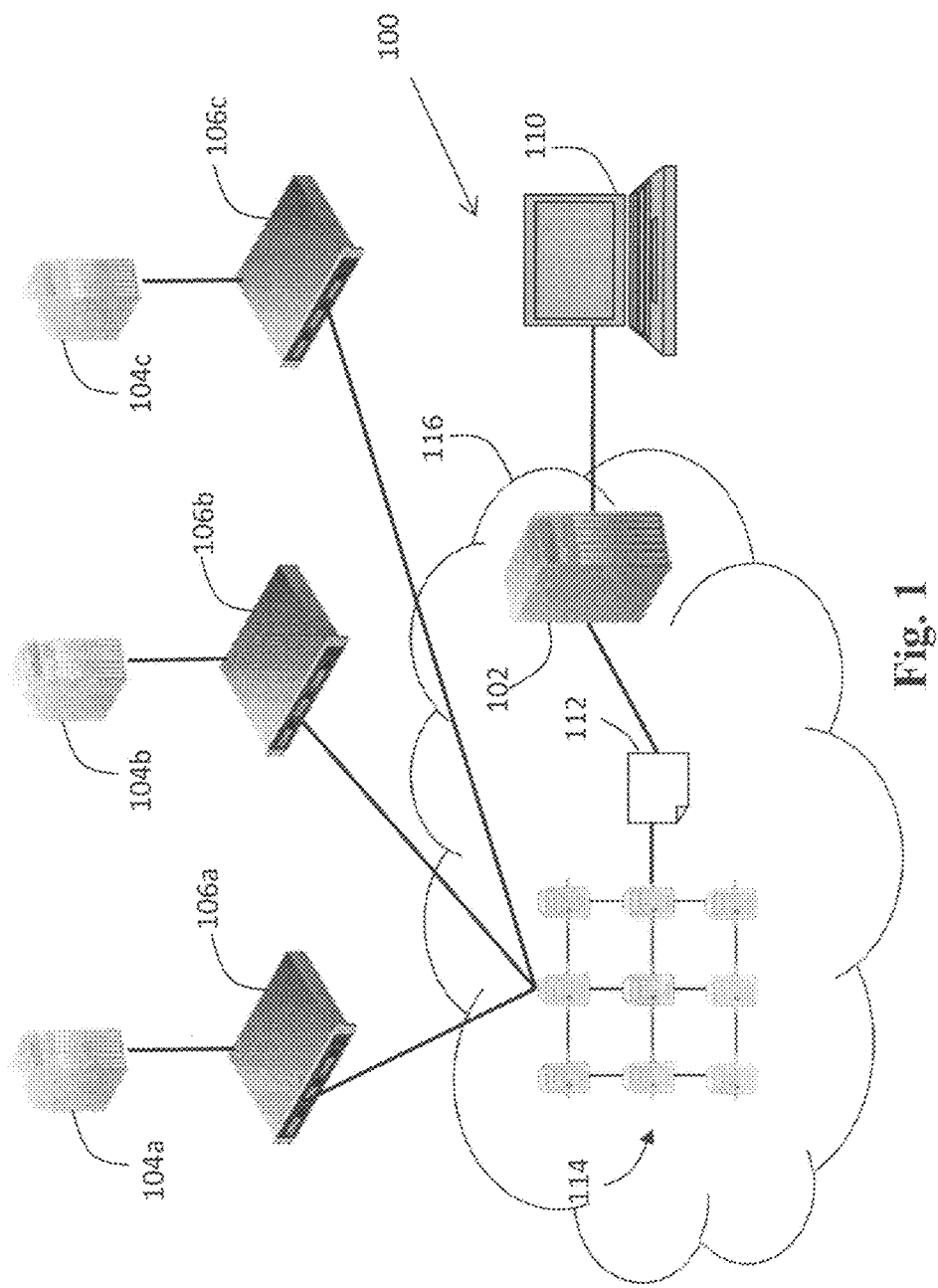
FIG. 1 illustrates an example system for measuring healthcare quality.

FIG. 1 illustrates an example system 100 for measuring healthcare quality. For illustrative purposes, many of the examples presented in this disclosure will be drawn to the management of healthcare data. However, it should be understood that this disclosure is not limited to a particular category of data, but it may be employed to manage any type of data that can be processed in the manner described herein.

Systems 100 leverages the power of parallel computing to process and analyze big data in hospital and ambulatory settings, giving end users access to real time data analytics for more accurate and efficient decision making. System 100 enables a user to efficiently measure the performance of healthcare providers and to monitor overall healthcare quality delivered by healthcare organizations in a holistic approach by aggregating, curating, and analyzing data from diverse and scattered data sources. System 100 includes a group or cluster of computers 114 having both processing capabilities as well as data storage capabilities for storing and processing healthcare data received from healthcare data suppliers 104a-c (herein after referred to as healthcare data supplier 104). Healthcare data supplier 104 is a data store comprising healthcare data and may be representative of various types of data stores located at different locations from which system 100 may receive healthcare data. For example, healthcare data supplier 104 may be a data store at a specific healthcare provider's office for storing patient data specific to the provider. Healthcare data supplier 104 may be a data store located at a hospital for storing data representative of patient data for multiple providers. Patient data include records of all interactions between patients and healthcare organizations, including but not limited to past doctor visits, scheduled upcoming visits, canceled visits, and "no shows" or scheduled visits for a patient who did not show up. In one example, healthcare data supplier 104 may also store and supply, to computer cluster 114, data relating to healthcare financial information, healthcare operational information, healthcare administrative data, and so on.

Computer cluster 114 is configured to receive healthcare data into a unified patient data file and to distribute the data, as subsets of the unified patient data file, across multiple computers within computer cluster 114. In one example, the data is distributed across the cluster using Hadoop and Hadoop Distributed FileSystem (HDFS).

System 100 has health data gateways 106a-c (hereinafter referred to as health data gateway 106) for retrieving healthcare data from healthcare data supplier 104 and for transferring the data to computer cluster 114. In one example, health data gateway 106 does not modify the retrieved healthcare data prior to transferring the data to computer cluster 114. In other words, healthcare data received at computer cluster 114 initially mirrors the data stored at healthcare data supplier 104. In one example, health data gateway 106 retrieves and transfers data according to a predefined schedule. For example, a user may configure health data gateway 106 to automatically run every night at a specific time. In one example, a user may manually trigger health data gateway 106 to retrieve and transfer data. In one example, health data gateway 106 may be configured to operate within a healthcare provider's firewall.

Different healthcare data suppliers 104a-c may store data in various forms. Thus, in order to compare and analyze the received data at computer cluster 114, data is curated after it is received. Specifically, the data received from the different healthcare data suppliers 104a-c is converted into a common format. In addition, the data is indexed so as to be readily searchable. The data may be indexed according to an established protocol, or according to a dynamic protocol. Once data at computer cluster 114 is curated and indexed, the data is ready to be analyzed in order to provide a user with a holistic view of healthcare quality.

The computers of computer cluster 114 are configured to execute program logic to process the curated and indexed healthcare data. Specifically, computer cluster 114 includes a measure engine (not shown) configured to calculate healthcare quality measures and to attribute patient encounters. In one example, computer cluster 114 is configured to execute the multiple instances of the measure engine in a distributed form via MapReduce.

The cluster of computers 114 are configured to operate in parallel to perform patient attributions and measure calculations efficiently such that the number of patients or datapoints received from healthcare data supplier 104 is not a rate-limiting factor. Computer cluster 114 is configured to receive a MapReduce job request and to distribute the request across multiple computers of computer cluster 114. Each computer, or node, having a subset of the unified patient data file, is capable of independently attributing patient data and calculating quality measures. Computer cluster 114 is configured to combine the results generated by the individual nodes of computer cluster 114 into a single set of measure results and to store the results in a measure data store 112.

By executing the measure engine on the worker nodes, computer cluster 114 is able to efficiently attribute patient data and to calculate quality measures of the unified patient data file. The measure engine executing on the worker nodes are also configured to output a series of measure and physician key pairs along with a measure value for the specific subset of the unified patient data file assigned to the particular worker node. Computer cluster 114 is configured to collect the results from the multiple worker nodes and combine the results to produce quality measure values for the entire unified patient data file.

System 100 has an application server 102 including a measure application program (not shown) that is configured to provide a user interface for allowing a user to interact with and analyze patient data. The measure application is configured to access the combined results stored in measure data store 112 in response to receiving user requests via user computer 110.

In an example embodiment, the measure application program on application server 102 as well as the data stored on computer cluster 114 is configured as cloud services accessible on cloud 116 by a user via a user computer 110. Thus, a user is able to measure and compare the performance of multiple healthcare providers and to monitor overall healthcare quality delivered by a healthcare organization, using common data rules and definitions, from a single integrated point, rather than accessing multiple data sources and having to work with multiple data formats.

Users accessing application server 102 via user computer 110 may include healthcare providers and healthcare administrators from within a healthcare organization, as well as users from outside the healthcare organization such as insurance providers, drug manufactures, researchers, etc. A user's access level may be determined by accesses credentials granted to the user by a systems administrator. For example, a healthcare provider may have limited access to healthcare data while an administrator of a healthcare organization may have expanded access to the data.

It should be understood that user computer 110 may include various forms of digital computers, including laptops, desktops, handheld computers, tablet computers, servers, and other similar types of computing devices.

Figure 2:
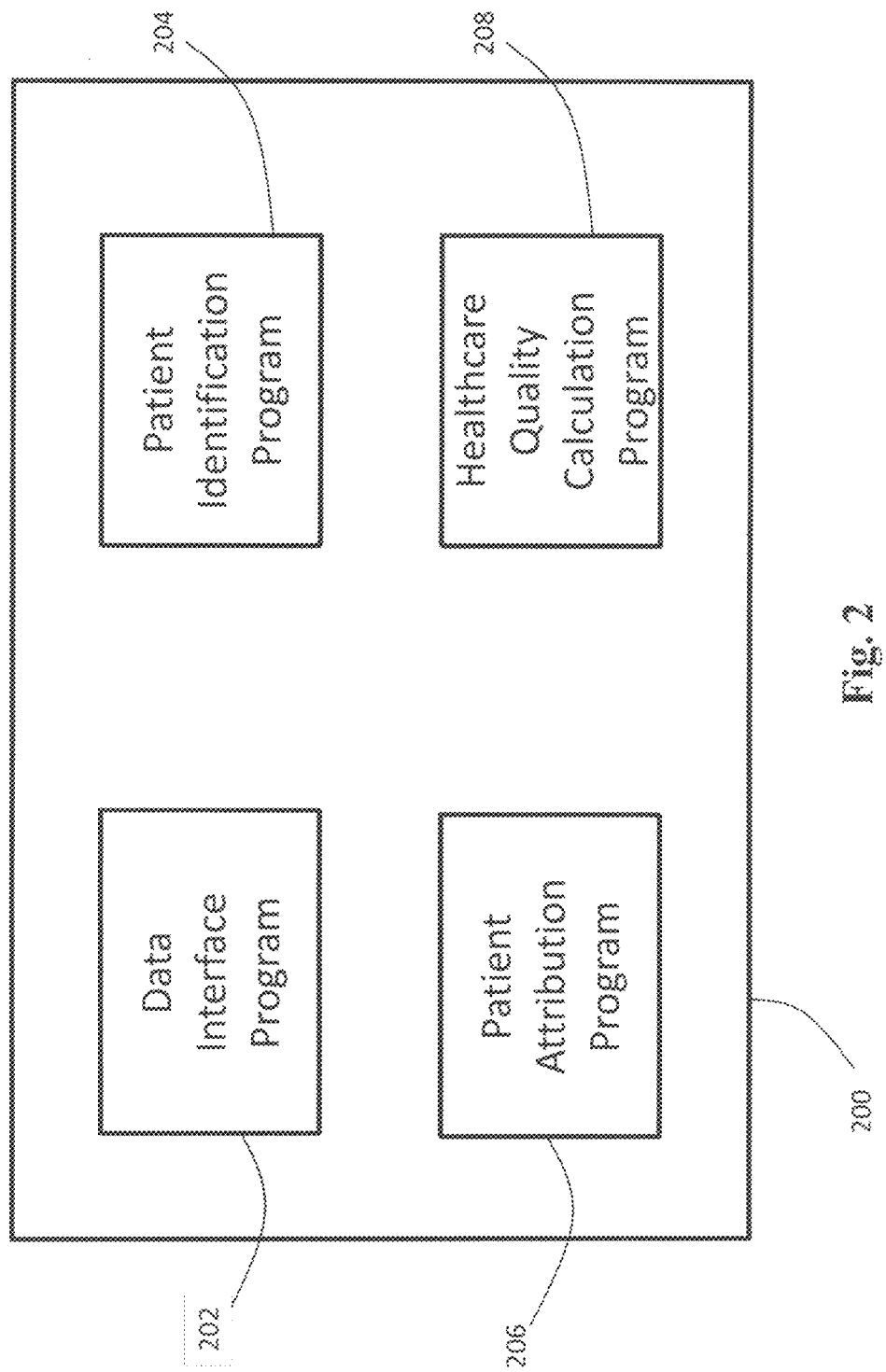
FIG. 2 is a block diagram of an example measure engine measuring healthcare quality.

FIG. 2 is a block diagram of an example measure engine 200, as described in FIG. 1. Measure engine 200 has a data interface program 202 for receiving a patient dataset and a healthcare quality measure definition. A healthcare quality measure definition includes a numerator and a denominator. The numerator represents a first type of patient encounter and the denominator represents a second type of patient encounter. For example, a second encounter type may be defined as all patients who have been diagnosed with high blood pressure. A first encounter type may be defined as all patients who have been prescribed a specific medication for treating high blood pressure. Thus, a healthcare quality measure may be defined to identify the number of patients who have been diagnosed with high blood pressure by a provider and who the provider has treated appropriately.

In one example, data interface program 202 may retrieve a predefined healthcare quality measure definition stored in computer cluster 114. In one example, data interface program 202 may be configured to receive a user defined healthcare quality measure. In such an example, a measure application program on application server 102 may be configured to enable the user to define the healthcare quality measure definition. In either case, the measure application program on application server 102 may be configured to enable the user to modify a healthcare quality measure definition. For example, a user may wish to adjust a healthcare quality measure definition to include patient encounters over a two year period instead of a one year period for which the definition may have been originally defined.

Measure engine 200 also has a patient identification program 204 for identifying, in patient data that correspond to the measure definition. For example, patient identification program 204 may identify all patient data for a selected time period during which a patient was diagnosed with high blood pressure and treated appropriately.

Measure application 200 also has a patient attribution program 206 for attributing patient data to a provider, based on an attribution rule. Attribution is a process of assigning one or more providers as being accountable for the cost and quality of care of a patient, regardless of which provider actually delivered healthcare services during the patient encounters. For example, a patient may regularly visit a primary care physician. The patient may also have visited a heart specialist, for example, based on a referral from the primary care physician. Depending on the attribution rule being followed, the patient may be attributed to either the primary care physician or the heart specialist, or both.

In one example, patient attribution program 206 is configured to filter identified patient data based on a predefined patient encounter status. Patient encounter status includes a canceled doctor's appointment, a doctor's appointments for which the patient did not show up, a scheduled doctor's appointment, a completed doctor's appointment, and so on. Patient attribution program 206 may also be configured to filter patient data based on a predefined patient encounter type. Patient encounter type includes inpatient encounters, outpatient encounters, emergency room encounters, and so on.

In on example, patient attribution program 206 is configured to identify a provider to whom a patient encounter is attributed according to a provider selection rule. A provider selection rule may include selecting the provider who most recently provided healthcare services to the patient, selecting the provider who first provided healthcare services to the patient, selecting the provider who most frequently provides healthcare services to the patient, and so on.

In one example, patient attribution program 206 is configured to validate a provider according to provider validation rule, before attributing a patient to the provider. Validating a provider may include analyzing the provider's specialty, role, title, and so on. For example, a user may define a validation rule to specify that patients may only be attributed to primary care physicians.

In one example, attribution rules may be modifiable. For example, a measure application program on application server 102 may be configured to provide a user with a user interface to enable the user to define and modify the attribution rules.

Measure engine 200 also has a healthcare quality calculation program 208 for calculating a healthcare quality measure for a provider, according to a healthcare quality measure definition, based on attributed patient data. Calculating a healthcare quality measure includes counting the number of identified patient encounters attributed to the provider, for both the numerator (first encounter type) and the denominator (second encounter type) and dividing the numerator by the denominator to produce a healthcare quality measure. For example, a healthcare quality measure of 80% for a specific measure definition related to high blood pressure treatment may indicate that a given provider successfully treated patients diagnosed with high blood pressure 80% of the time.

In one example, healthcare quality measure program 208 may be configured to count the number of distinct patients associated with the identified subset of attributed patient encounters, rather than identifying the actual number of encounters, in order to avoid double counting a patient. For example, a user may decide to count only once, a patient who was mistreated or misdiagnosed two or more times for high blood pressure within a certain period of time. Thus, the two encounters would be defined as a single occurrence, for the purpose of measuring healthcare quality. Alternatively, a user may decide to include the same patient in the healthcare quality measure, more than one time if the two or more encounters in which the same patient was mistreated or misdiagnosed for high blood pressure occurred outside a predefined time frame. For example, a user may decide to include the same patient in the healthcare quality measure twice if the patient was mistreated one time in January 2010 and was again mistreated in January 2012. These encounters may be considered separate occurrences for the purpose of measuring healthcare quality.

Figure 3:
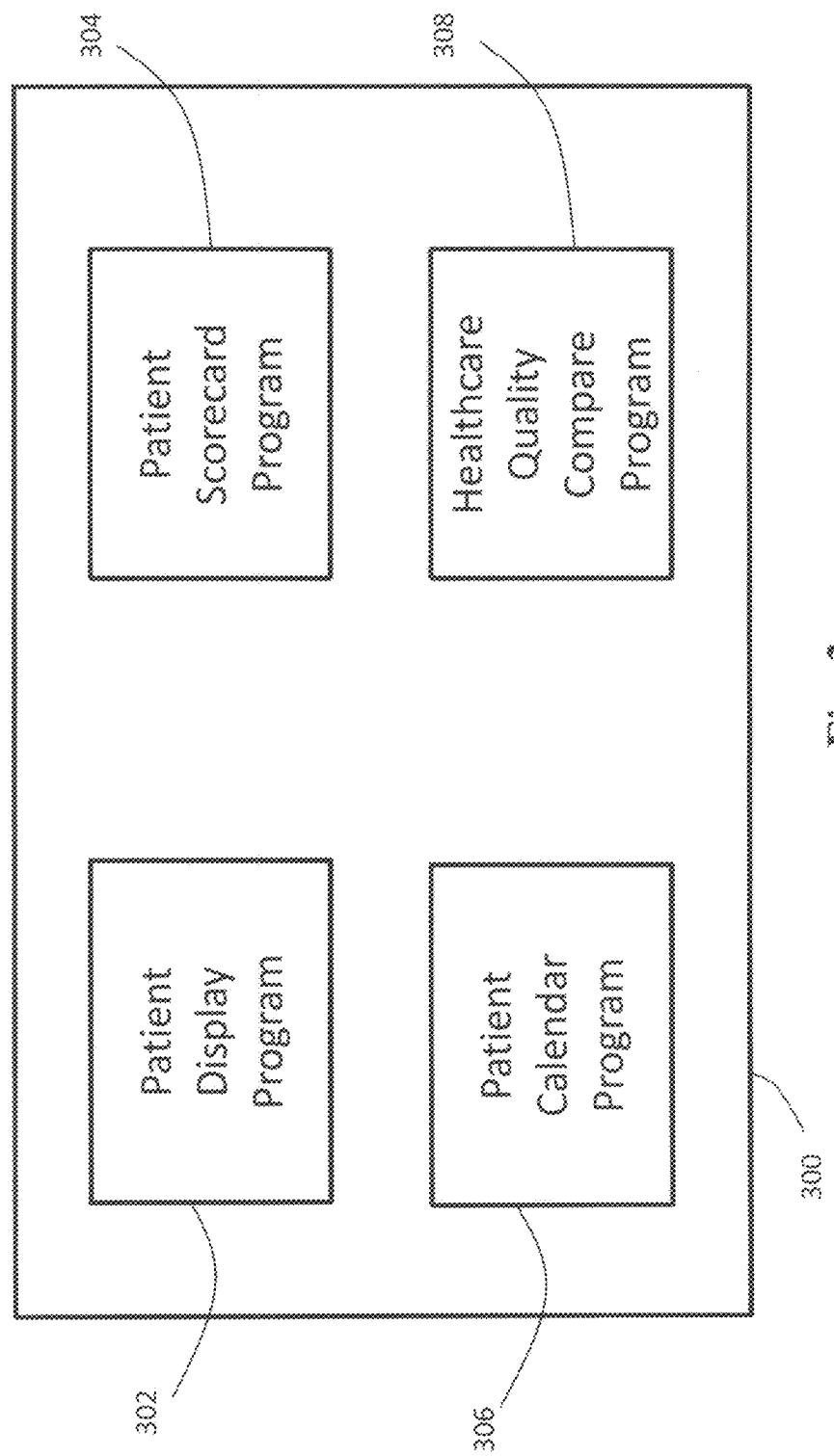
FIG. 3 is a block diagram of an example measure application program for enabling a user to interact with and analyze patient data.

FIG. 3 is a block diagram of an example measure application program 300, as described in FIG. 1, for enabling a user to interact with and analyze patient data, via application server 102. Measure application program 300 has a patient display program 302 configured for displaying one or more healthcare quality measures that have been calculated for a specific provider. In one example, a user may select one of the healthcare quality measures being displayed in order to view the patients who were used to calculate that measure. Accordingly, patient display program 302 may be configured to provide a user with a user interface for displaying a list of patients associated with the encounters who were used to calculate a healthcare quality measure for a specific provider in response to the user selecting a healthcare quality measure.

Measure application program 300 has a patient scorecard program 304 configured for displaying a patient scorecard. A patient scorecard displays the items or types of encounters for which providers are given healthcare quality measures and indicates whether the particular patient has passed or not. For example, if a provider is given a healthcare quality measure for the number of patients successfully diagnosed and treated with high blood pressure, a patient may have an item on his patient scorecard indicating whether or not the patient was successfully treated for high blood pressure. A green check mark, for example, may indicate that the patient was successfully treated for high blood pressure while a red "X" may indicate that the patient was not successfully treated for high blood pressure. In one example, the patient's scorecard may also indicate, with a "n/a," that the item or measure does not apply to the patient.

Measure application 300 may be configured to enable a user to access a specific patient's scorecard by selecting a patient from a list of patients being displayed via patient display program 302. Alternatively, patient scorecard program 304 may be configured to enable a user to directly search and access a specific patient's scorecard by name, by patient number, and so on.

Once a patient is identified, either by searching for the patient using a search function or by selecting a patient from a list of patients, patient scorecard program 304 is configured to create a patient scorecard by determining, for each healthcare quality measure, whether the patient is associated with a numerator representative of a first encounter definition of a corresponding healthcare quality measure definition and whether the patient is associated with a denominator representative of a second encounter definition of the corresponding healthcare quality measure definition.

Measure application program 300 has a patient calendar program 306 configured for displaying a calendar of scheduled upcoming patient visits and for indicating whether any of the patients scheduled for the upcoming visits fail any of the items or measures of the patient scorecard, as discussed above. In other words, patient calendar program 306 is configured to notify a user if a patient scheduled for an upcoming visit is associated with a denominator representative of a second encounter definition of a corresponding healthcare quality measure definition but is not associated with a numerator representative of a first encounter definition of a corresponding healthcare quality measure definition. For example, if a certain patient scheduled for an upcoming visit with a provider has been determined to have high blood pressure but has not been treated for high blood pressure, patient calendar program 306 may alert or notify the provider of the upcoming patient visit.

In one example, measure application program 300 is configured to enable a user to view healthcare quality measures at an organizational level as well as for individual providers. This allows the user to achieve a holistic view of healthcare quality within an organization as well as compare healthcare quality measures of individual doctors to healthcare quality measures of other doctors or healthcare quality measures of the organization as a whole.

To achieve such a holistic view of an organization, data interface program 202 of measure engine 200 is configured to receive data representative of an organizational structure. The organizational structure defines groups of healthcare providers within an organization. For example, a certain hospital may be type of group. Or, a certain specialty, such as pediatrics, may be defined as group as well. Patient attribution program 206 is configured to associate providers with at least one group according to the organizational structure. Healthcare quality calculation program 208 is configured to calculate healthcare quality measures for the groups of healthcare providers, based on calculated healthcare quality measures for the individual providers.

Measure application program 300 has a healthcare quality compare program 308 configured for comparing healthcare quality measures of individual providers with those of other providers as well as with groups of providers according to the organizational structure. In response to receiving a selection of a provider and a group of providers, healthcare quality compare program 308 is configured to generate a comparison of healthcare quality measures for the selected group with healthcare quality measure for the selected provider.

Figure 4:
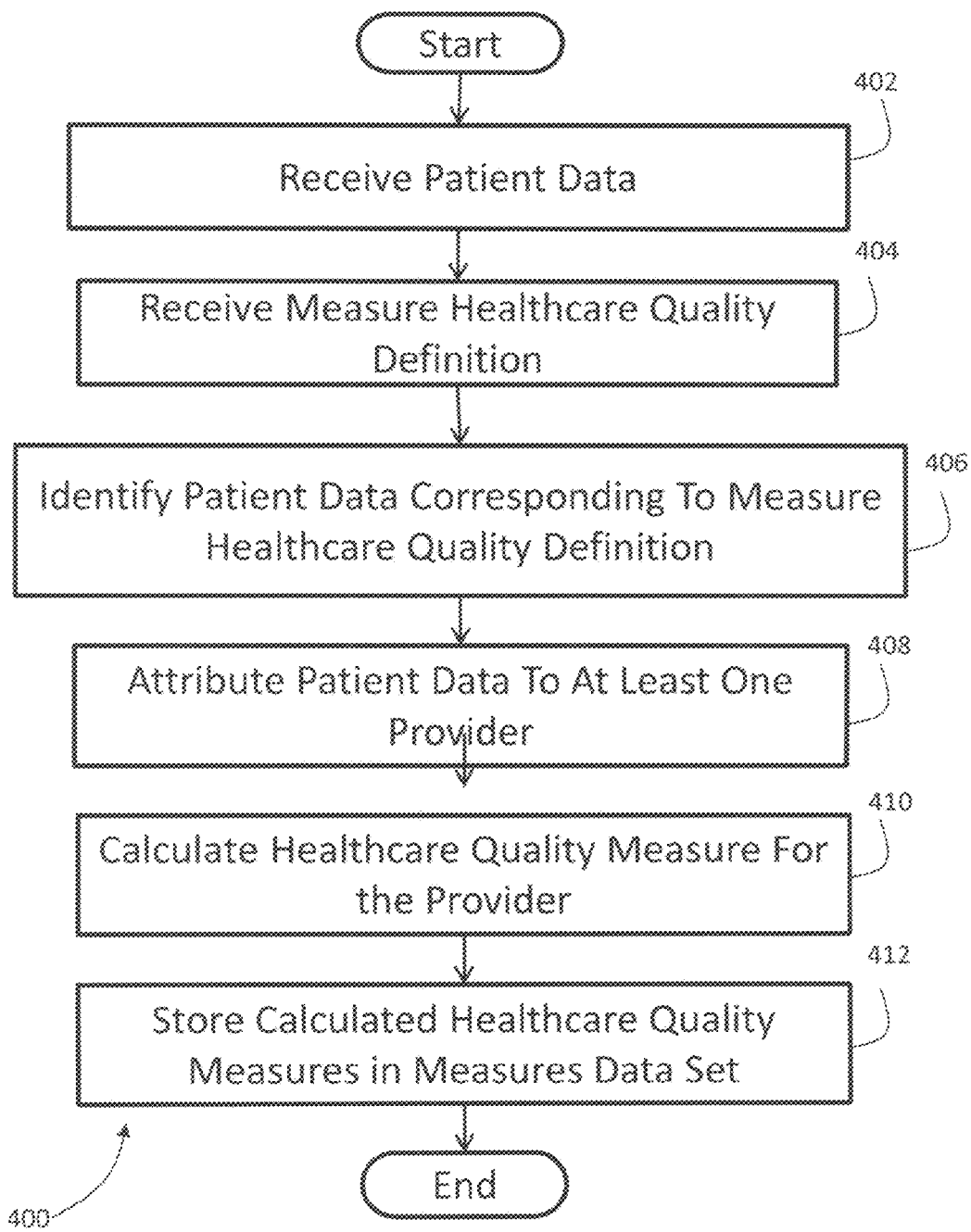
FIG. 4 is a flow chart illustrating an example method for measuring healthcare quality.

FIG. 4 is a flow chart illustrating an example method 400 for measuring healthcare quality. At step 402, interface program 200 receives a patient dataset representative of patients within a healthcare organization. At step 404, data interface program 202 receives a healthcare quality measure definition including a numerator that defines a first encounter and a denominator that defines a second encounter. At step 406, patient identification program 204 identifies patient data that corresponds to the measure definition. At step 408, patient attribution program 206 attributes the identified patient data to a provider based on an attribution rule. At step 410, healthcare quality calculation program calculates a healthcare quality measure for the provider, according to the healthcare quality measure definition, based on the attributed patient encounter. At step 412, data interface program 202 stores calculated healthcare quality measures in measures data store 112.

In one example, the steps of method 400 may be performed automatically according to a predefined schedule. For example, measure engine 200 may perform the steps of method 400 every day at 8 AM. In another example, the steps of method 400 may be performed by measure engine 200 in response to user initiated action via a measure application program 300 on application server 102.

Figure 5:
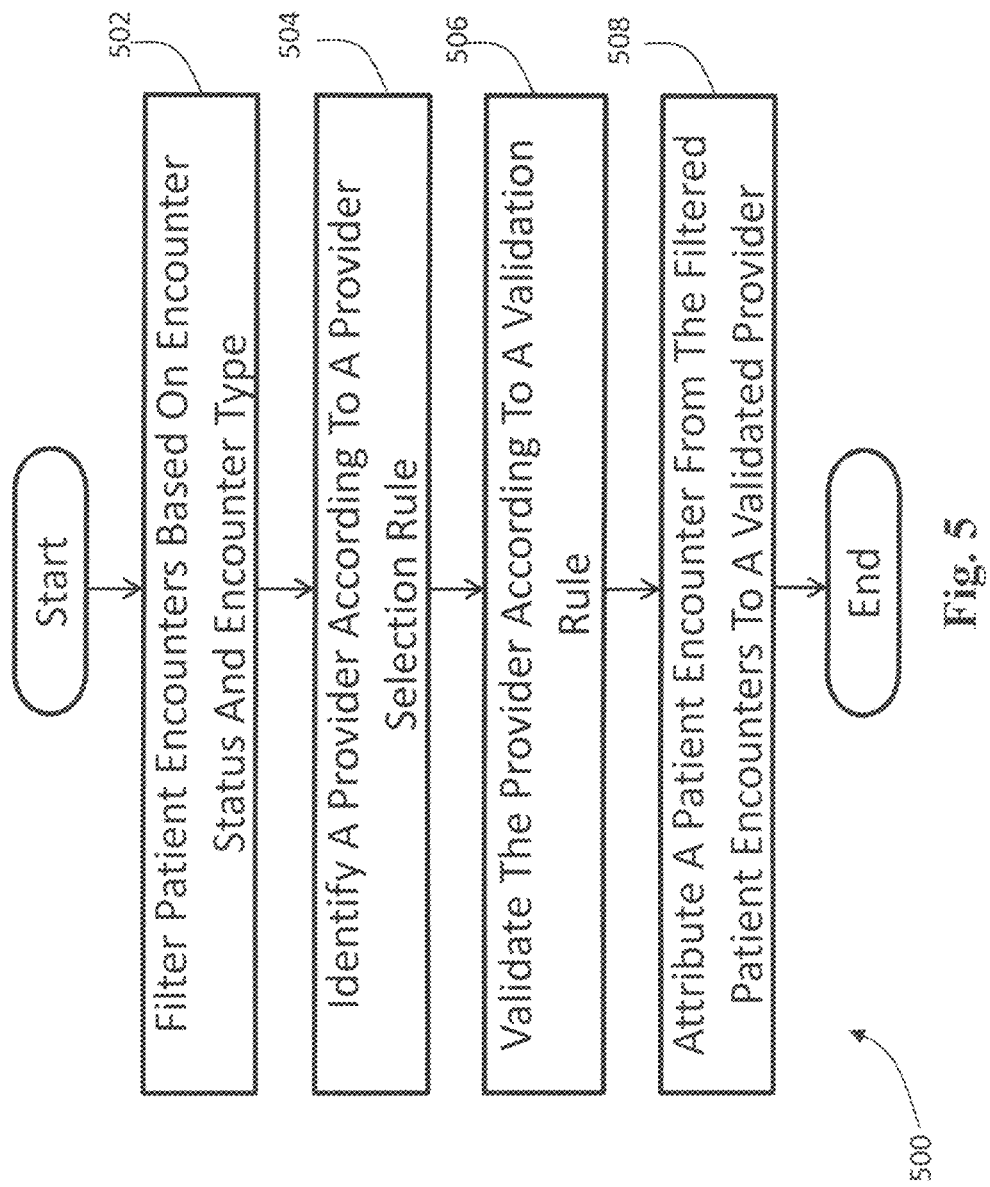
FIG. 5 is a flow chart illustrating an example method for attributing patient encounters to a provider.

FIG. 5 is a flow chart illustrating an example method for attributing patient data to a provider. At step 502, patient attribution program 206 filters identified patient data based on at least one of a predefined encounter status and a predefined encounter type. At step 504, patient attribution program 206 identifies at least one provider to attribute at least one patient encounter of the filtered patient data to, according to a provider selection rule. At step 506, patient attribution program 206 validates the at least one identified provider according to a provider validation rule. At step 508, patient attribution program 206 attributes the at least one patient encounter of the filtered patient encounters to the at least one validated provider.

While for purposes of simplicity of explanation, the illustrated methodologies are shown and described as a series of blocks, it is to be appreciated that the methodologies are not limited by the order of the blocks, as some blocks can occur in different orders or concurrently with other blocks from that shown or described. Moreover, less than all the illustrated blocks may be required to implement an example methodology. Furthermore, additional or alternative methodologies can employ additional, not illustrated blocks.

In the flow diagram, blocks denote "processing blocks" that may be implemented with logic. The processing blocks may represent a method step or an apparatus element for performing the method step. A flow diagram does not depict syntax for any particular programming language, methodology, or style (e.g., procedural, object-oriented). Rather, a flow diagram illustrates functional information one skilled in the art may employ to develop logic to perform the illustrated processing. It will be appreciated that in some examples, program elements like temporary variables, routine loops, and so on, are not shown. It will be further appreciated that electronic and software applications may involve dynamic and flexible processes so that the illustrated blocks can be performed in other sequences that are different from those shown or that blocks may be combined or separated into multiple components. It will be appreciated that the processes may be implemented using various programming approaches like machine language, procedural, object oriented or artificial intelligence techniques.

In one example, methodologies are implemented as processor executable instructions or operations provided on a computer-readable medium. While the above method is described as being provided on a computer-readable medium, it is to be appreciated that other example methods described herein can also be provided on a computer-readable medium.

While FIGS. 4 and 5 illustrate various actions occurring in serial, it is to be appreciated that various actions illustrated in FIGS. 4 and 5 could occur substantially in parallel. While four processes are described, it is to be appreciated that a greater or lesser number of processes could be employed and that lightweight processes, regular processes, threads, and other approaches could be employed. It is to be appreciated that other example methods may, in some cases, also include actions that occur substantially in parallel.

Figure 6:
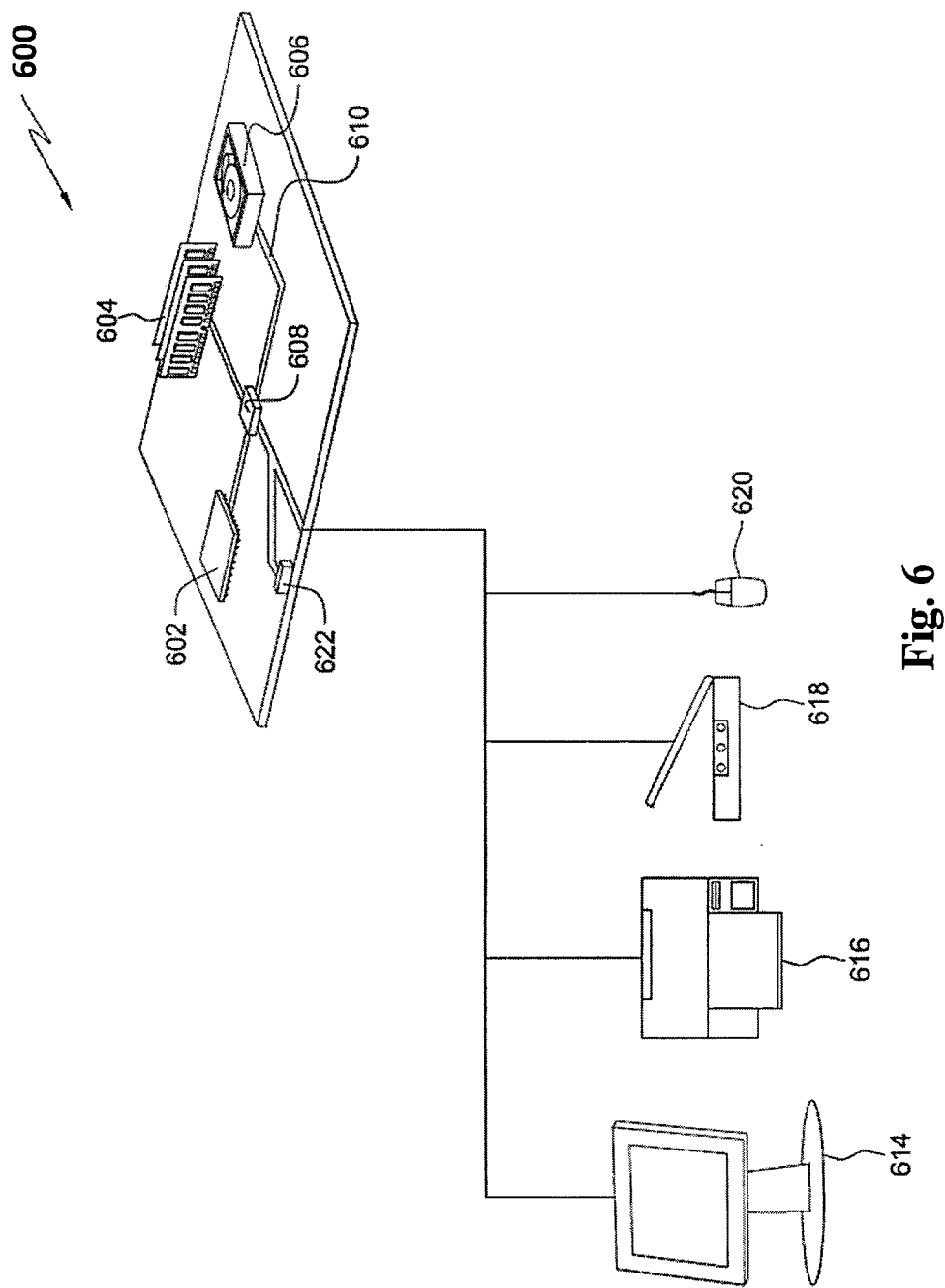
FIG. 6 is a block diagram of an example computer for implementing an example system for measuring healthcare quality.

FIG. 6 is a block diagram of an example computer 600, i.e. an application server 102 or a computer of a computer cluster 114, as descried in FIG. 1, for implementing the system and method for measuring healthcare quality. The example computer 600 is intended to represent various forms of digital computers, including laptops, desktops, handheld computers, tablet computers, servers, and other similar types of computing devices. Computer 600 includes a processor 602, memory 604, a storage device 606, and a communication port 622, operably connected by an interface 608 via a bus 610.

Storage device 606 can store at least one of measure engine 200 and measure application program 300.

Processor 602 processes instructions, via memory 604, for execution within computer 600, including measure engine 200 and measure application program 300 stored on storage device 606. In an example embodiment, multiple processors along with multiple memories may be used. In an example embodiment, multiple application servers 102 may be connected, with each device providing portions of the necessary operations.

Memory 604 may be volatile memory or non-volatile memory. Memory 604 may be a computer-readable medium, such as a magnetic disk or optical disk. Storage device 606 may be a computer-readable medium, such as floppy disk devices, a hard disk device, optical disk device, a tape device, a flash memory, or other similar solid state memory device, or an array of devices, including devices in a storage area network of other configurations. A computer program product can be tangibly embodied in a computer readable medium such as memory 604 or storage device 606. The computer program product may contain measure engine 200 and measure application program 300.

Computer 600 can be coupled to one or more input and output devices such as a display 614, a printer 616, a scanner 618, and a mouse 620.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

The following includes definitions of selected terms employed herein. The definitions include various examples, forms, or both of components that fall within the scope of a term and that may be used for implementation. The examples are not intended to be limiting. Both singular and plural forms of terms may be within the definitions.

"Computer communication," as used herein, refers to a communication between two or more computing devices (e.g., computer, personal digital assistant, cellular telephone) and can be, for example, a network transfer, a file transfer, an applet transfer, an email, a hypertext transfer protocol (HTTP) transfer, and so on. A computer communication can occur across, for example, a wireless system (e.g., IEEE 802.11, IEEE 802.15), an Ethernet system (e.g., IEEE 802.3), a token ring system (e.g., IEEE 802.5), a local area network (LAN), a wide area network (WAN), a point-to-point system, a circuit switching system, a packet switching system, combinations thereof, and so on.

"Computer-readable medium," as used herein, refers to a medium that participates in directly or indirectly providing signals, instructions, or data. A computer-readable medium may take forms, including, but not limited to, non-volatile media, volatile media, and transmission media. Non-volatile media may include, for example, optical or magnetic disks, and so on. Volatile media may include, for example, optical or magnetic disks, dynamic memory, and the like. Transmission media may include coaxial cables, copper wire, fiber optic cables, and the like. Transmission media can also take the form of electromagnetic radiation, like that generated during radio-wave and infra-red data communications, or take the form of one or more groups of signals. Common forms of a computer-readable medium include, but are not limited to, a floppy disk, a flexible disk, a hard disk, a magnetic tape, other magnetic media, a CD-ROM, other optical media, punch cards, paper tape, other physical media with patterns of holes, a RAM, a ROM, an EPROM, a FLASH-EPROM, or other memory chip or card, a memory stick, a carrier wave/pulse, and other media from which a computer, a processor, or other electronic device can read. Signals used to propagate instructions or other software over a network, like the Internet, can be considered a "computer-readable medium."

"Data store," as used herein, refers to a physical or logical entity that can store data. A data store may be, for example, a database, a table, a file, a list, a queue, a heap, a memory, a register, and so on. A data store may reside in one logical or physical entity or may be distributed between two or more logical or physical entities.

"Logic," as used herein, includes but is not limited to hardware, firmware, software, or combinations of each to perform a function(s) or an action(s), or to cause a function or action from another logic, method, or system. For example, based on a desired application or needs, logic may include a software controlled microprocessor, discrete logic like an application specific integrated circuit (ASIC), a programmed logic device, a memory device containing instructions, or the like. Logic may include one or more gates, combinations of gates, or other circuit components. Logic may also be fully embodied as software. Where multiple logical logics are described, it may be possible to incorporate the multiple logical logics into one physical logic. Similarly, where a single logical logic is described, it may be possible to distribute that single logical logic between multiple physical logics.

An "operable connection," or a connection by which entities are "operably connected," is one in which signals, physical communications, or logical communications may be sent or received. Typically, an operable connection includes a physical interface, an electrical interface, or a data interface, but it is to be noted that an operable connection may include differing combinations of these or other types of connections sufficient to allow operable control. For example, two entities can be operably connected by being able to communicate signals to each other directly or through one or more intermediate entities like a processor, operating system, a logic, software, or other entity. Logical or physical communication channels can be used to create an operable connection.

"Signal," as used herein, includes but is not limited to one or more electrical or optical signals, analog or digital signals, data, one or more computer or processor instructions, messages, a bit or bit stream, or other means that can be received, transmitted, or detected.

"Software," as used herein, includes but is not limited to, one or more computer or processor instructions that can be read, interpreted, compiled, or executed and that cause a computer, processor, or other electronic device to perform functions, actions, or behave in a desired manner. The instructions may be embodied in various forms like routines, algorithms, modules, methods, threads, or programs including separate applications or code from dynamically or statically linked libraries. Software may also be implemented in a variety of executable or loadable forms including, but not limited to, a stand-alone program, a function call (local or remote), a servelet, an applet, instructions stored in a memory, part of an operating system, or other types of executable instructions. It will be appreciated by one of ordinary skill in the art that the form of software may depend, for example, on requirements of a desired application, the environment in which it runs, or the desires of a designer/programmer or the like. It will also be appreciated that computer-readable or executable instructions can be located in one logic or distributed between two or more communicating, co-operating, or parallel processing logics and thus can be loaded or executed in serial, parallel, massively parallel, and other manners.

Suitable software for implementing the various components of the example systems and methods described herein may be produced using programming languages and tools like Java, Java Script, Java.NET, ASP.NET, VB.NET, Cocoa, Pascal, C#, C++, C, CGI, Perl, SQL, APIs, SDKs, assembly, firmware, microcode, or other languages and tools. Software, whether an entire system or a component of a system, may be embodied as an article of manufacture and maintained or provided as part of a computer-readable medium as defined previously. Another form of the software may include signals that transmit program code of the software to a recipient over a network or other communication medium. Thus, in one example, a computer-readable medium has a form of signals that represent the software/firmware as it is downloaded from a web server to a user. In another example, the computer-readable medium has a form of the software/firmware as it is maintained on the web server. Other forms may also be used.

"User," as used herein, includes but is not limited to one or more persons, software, computers or other devices, or combinations of these.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

Some portions of the detailed descriptions are presented in terms of algorithms and symbolic representations of operations on data bits within a memory. These algorithmic descriptions and representations are the means used by those skilled in the art to convey the substance of their work to others. An algorithm is here, and generally, conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic and the like.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

The invention claimed is:

1. A method for measuring healthcare quality, the method comprising the steps of:
   a plurality of computers receiving a patient dataset in a plurality of different formats representative of patients within a healthcare organization, wherein the plurality of computers form a computer cluster and operate in parallel;
   the plurality of computers converting the patient dataset from the plurality of different formats to a common format and indexing the patient dataset to be searchable;
   the plurality of computers distributing the patient dataset across the plurality of computers as subsets of patient datasets;

the plurality of computers receiving at least one healthcare quality measure definition comprising a numerator and a denominator each representing a quantity of patients;

each of the plurality of computers independently identifying, in the subsets of patient datasets, patient data that corresponds to the measure definition;

each of the plurality of computers independently attributing the identified patient data to at least one provider based on an attribution rule;

each of the plurality of computers independently calculating a quantity of distinct patients for the numerator and denominator for at least one healthcare quality measure for the at least one provider, according to the healthcare quality measure definition, to determine the at least one healthcare quality measure based on the attributed patient data, wherein a plurality of a same patient within the attributed patient data is consolidated by the plurality of computers to a single patient for determining the quantity of patients for the numerator and denominator based on occurrence of a plurality of encounters for a same medical condition between a provider and the same patient within a time period; and the plurality of computers combining results from the plurality of computers to calculate the at least one healthcare quality measure and storing the at least one calculated healthcare quality measure in a measure dataset.

2. The method of claim 1, further comprising the steps of:
a computer accessing the measure dataset to identify at least one patient associated with the attributed patient data; and
the computer outputting data representative of the at least one patient.

3. The method of claim 2, wherein the step of the computer identifying at least one patient comprises the computer identifying a plurality of patients, and wherein the method further comprises the steps of:
the computer receiving data representative of a patient selected from the plurality of patients; and
the computer determining, for each of a plurality of healthcare quality measures having corresponding healthcare quality measure definitions, whether the patient is associated with a numerator representative of a first encounter definition of a corresponding healthcare quality measure definition and whether the patient is associated with a denominator representative of a second encounter definition of the corresponding healthcare quality measure definition.

4. The method of claim 1, further comprising the steps of:
a computer accessing the measure dataset to identify at least one patient scheduled for a future patient encounter with a selected provider;
the computer determining whether the patient is associated with a numerator representative of a first encounter definition of a corresponding healthcare quality measure definition and whether the patient is associated with a denominator representative of a second encounter definition of a corresponding healthcare quality measure definition; and
the computer generating a notification responsive to determining that the patient is not associated with the numerator of the corresponding healthcare quality measure definition and that the patient is associated with the denominator of the corresponding healthcare quality measure definition.

5. The method of claim 1, wherein the step of each of the plurality of computers independently attributing the identified patient data to at least one provider based on an attribution rule, comprises the steps of:
the plurality of computers filtering the identified patient data based on at least one of a predefined patient encounter status and a predefined patient encounter type;
the plurality of computers identifying at least one provider to attribute at least one patient encounter of the filtered patient data to, according to a provider selection rule;
the plurality of computers validating the at least one identified provider according to a provider validation rule; and
the plurality of computers attributing the at least one patient encounter of the filtered patient data to the at least one validated provider.

6. The method of claim 1, further comprising the steps of:
the plurality of computers receiving data representative of an organizational structure, wherein the organizational structure defines a plurality of groups of healthcare providers;
the plurality of computers associating the at least one provider with at least one of the plurality of groups of healthcare providers according to the organizational structure; and
the plurality of computers calculating at least one healthcare quality measure for each of the groups of the plurality of groups of healthcare providers, based on the at least one calculated healthcare quality measure for the at least one provider.

7. The method of claim 6, further comprising the steps of:
a computer receiving a selection of at least one provider;
the computer receiving a selection of at least one group of the plurality of groups of providers; and
the computer accessing the measure dataset to generate a comparison of at least one healthcare quality measure for the at least one selected group with at least one healthcare quality measure for the at least one selected provider.

8. A system for measuring healthcare quality, the system comprising:
a plurality of computers operating in parallel, wherein each of the computers comprises at least one processor and at least one computer-readable tangible storage device including program instructions that are executed by the at least one processor, and wherein the program instructions are configured to cause the plurality of computers to:
receive a patient dataset in a plurality of different formats representative of patients within a healthcare organization;
convert the patient dataset from the plurality of different formats to a common format and index the patient dataset to be searchable;
distribute the patient dataset across the plurality of computers as subsets of patient datasets;
receive at least one healthcare quality measure definition comprising a numerator representative of a first patient encounter definition and a denominator representative of a second patient encounter definition, wherein the numerator and denominator each represent a quantity of patients;
independently identify in the subsets of patient datasets, via each of the plurality of computers, patient data that correspond to the measure definition;

independently attribute, via each of the plurality of computers, the identified patient data to at least one provider based on an attribution rule;

independently calculate, via each of the plurality of computers, a quantity of distinct patients for the numerator and denominator for at least one healthcare quality measure for the at least one provider, according to the healthcare quality measure definition, to determine the at least one healthcare quality measure based on the attributed patient data, wherein a plurality of a same patient within the attributed patient data is consolidated by the plurality of computers to a single patient for determining the quantity of patients for the numerator and denominator based on occurrence of encounters for a same medical condition between a provider and the same patient within a time period; and combine results from the plurality of computers to calculate the at least one healthcare quality measure and store the at least one calculated healthcare quality measure in a measure dataset.

9. The system of claim 8, wherein the program instructions cause the plurality of computers to:

identify at least one patient associated with the attributed patient data; and output data representative of the at least one patient.

10. The system of claim 9, wherein a plurality of patients associated with the attributed patient data are identified, and wherein the program instructions cause the plurality of computers to:

receive data representative of a patient selected from the plurality of patients; and determine, for each of a plurality of healthcare quality measures having corresponding healthcare quality measure definitions, whether the patient is associated with a numerator representative of a first encounter definition of a corresponding healthcare quality measure definition and whether the patient is associated with a denominator representative of a second encounter definition of the corresponding healthcare quality measure definition.

11. The system of claim 8, wherein the program instructions cause the plurality of computers to:

identify at least one patient scheduled for a future patient encounter with a selected provider;

determine whether the patient is associated with a numerator representative of a first encounter definition of a corresponding healthcare quality measure definition and to determine whether the patient is associated with a denominator representative of a second encounter definition of a corresponding healthcare quality measure definition; and generate a notification responsive to determining that the patient is not associated with the numerator of the corresponding healthcare quality measure definition and that the patient is associated with the denominator of the corresponding healthcare quality measure definition.

12. The system of claim 8, wherein the program instructions cause the plurality of computers to:

filter the identified patient data based on at least one of a predefined patient encounter status and a predefined patient encounter type;

identify at least one provider to attribute at least one patient encounter of the filtered patient data to, according to a provider selection rule;

validate the at least one identified provider according to a provider validation rule; and attribute the at least one patient encounter of the filtered patient data to the at least one validated provider.

13. The system of claim 8, wherein the program instructions cause the plurality of computers to:

receive data representative of an organizational structure, wherein the organizational structure defines a plurality of groups of healthcare providers;

associate the at least one provider with at least one of the plurality of groups of healthcare providers according to the organizational structure; and calculate at least one healthcare quality measure for each of the groups of the plurality of groups of healthcare providers, based on the at least one calculated healthcare quality measure for the at least one provider.

14. The system of claim 13, wherein the program instructions cause the plurality of computers to:

receive a selection of at least one provider, receive a selection of at least one group of the plurality of groups of providers; and generate a comparison of at least one healthcare quality measure for the at least one selected group with at least one healthcare quality measure for the at least one selected provider.

15. A computer program product for measuring healthcare quality, the computer program product comprising:

at least one non-transitory computer-readable tangible storage device and program instructions stored on the at least one storage device, the program instructions are configured to be executed by one or more processors of a plurality of computers operating in parallel to:

receive a patient dataset in a plurality of different formats representative of patients within a healthcare organization;

convert the patient dataset from the plurality of different formats to a common format and index the patient dataset to be searchable;

distribute the patient dataset across the plurality of computers as subsets of patient datasets;

receive at least one healthcare quality measure definition comprising a numerator representative of a first patient encounter definition and a denominator representative of a second patient encounter definition, wherein the numerator and denominator each represent a quantity of patients;

independently identify in the subsets of patient datasets, via each of the plurality of computers, patient data that correspond to the measure definition;

independently attribute, via each of the plurality of computers, the identified patient data to at least one provider based on an attribution rule;

independently calculate, via each of the plurality of computers, a quantity of distinct patients for the numerator and denominator for at least one healthcare quality measure for the at least one provider, according to the healthcare quality measure definition, to determine the at least one healthcare quality measure based on the attributed patient data, wherein a plurality of a same patient within the attribute patient data is consolidated by the plurality of computers to a single patient for determining the quantity of patients for the numerator and denominator based on occurrence of encounters for a same medical condition between a provider and the same patient within a time period; and combine results from the plurality of computers to calculate the at least one healthcare quality measure and store the at least one calculated healthcare quality measure in a measure dataset.

16. The computer program product of claim 15, wherein the program instructions are configured to be executed by the one or more processors of the plurality of computers to:
- identify at least one patient associated with the at least one attributed patient data; and
- display, on a display, the at least one patient.

17. The computer program product of claim 16, wherein the program instructions are configured to identify a plurality of patients associated with the attributed patient data, and wherein the program instructions are configured to be executed by the one or more processors of the plurality of computers to:
- receive data representative of a patient selected from the plurality of patients; and
- determine, for each of a plurality of healthcare quality measures having corresponding healthcare quality measure definitions, whether the patient is associated with a numerator representative of a first encounter definition of a corresponding healthcare quality measure definition and whether the patient is associated with a denominator representative of a second encounter definition of the corresponding healthcare quality measure definition.

18. The computer program product of claim 15, wherein the program instructions are configured to be executed by the one or more processors of the plurality of computers to:
- identify at least one patient scheduled for a future patient encounter with a selected provider;
- determine whether the patient is associated with a numerator representative of a first encounter definition of a corresponding healthcare quality measure definition and whether the patient is associated with a denominator representative of a first encounter definition of a corresponding healthcare quality measure definition; and
- generate a notification responsive to determining that the patient is not associated with the numerator of the corresponding healthcare quality measure definition and that the patient is associated with the denominator of the corresponding healthcare quality measure definition.

19. The computer program product of claim 15, wherein the program instructions are executed by the one or more processors of the plurality of computers to:
- filter the identified patient data based on at least one of a predefined patient encounter status and a predefined patient encounter type;
- identify at least one provider to attribute at least one patient encounter of the filtered patient data to, according to a provider selection rule;
- validate the at least one identified provider according to a provider validation rule; and
- attribute the at least one patient encounter of the filtered patient data to the at least one validated provider.

20. The computer program product of claim 15, wherein the program instructions are configured to be executed by the one or more processors of the plurality of computers to:
- receive data representative of an organizational structure, wherein the organizational structure defines a plurality of groups of healthcare providers;
- associate the at least one provider with at least one of the plurality of groups of healthcare providers according to the organizational structure; and
- calculate at least one healthcare quality measure for each of the groups of the plurality of groups of healthcare providers, based on the at least one calculated healthcare quality measure for the at least one provider.

* * * * *